(12) United States Patent
Bar-Cohen et al.

(10) Patent No.: US 9,907,961 B2
(45) Date of Patent: Mar. 6, 2018

(54) ARTIFICIAL CARDIAC PACEMAKER DEVICE ASSEMBLY

(71) Applicants: Yaniv Bar-Cohen, South Pasadena, CA (US); Ramen Chmait, La Cresenta, CA (US); Michael J. Silka, La Canada, CA (US); Mark Sklansky, Beverly Hills, CA (US)

(72) Inventors: Yaniv Bar-Cohen, South Pasadena, CA (US); Ramen Chmait, La Cresenta, CA (US); Michael J. Silka, La Canada, CA (US); Mark Sklansky, Beverly Hills, CA (US)

(73) Assignees: CHILDREN'S HOSPITAL LOS ANGELES, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 26 days.

(21) Appl. No.: 14/808,179

(22) Filed: Jul. 24, 2015

(65) Prior Publication Data

US 2015/0328453 A1  Nov. 19, 2015

Related U.S. Application Data

(62) Division of application No. 13/375,983, filed as application No. PCT/US2010/037557 on Jun. 5, 2010, now Pat. No. 9,126,047.

(Continued)

(51) Int. Cl.
*A61N 1/362* (2006.01)
*A61N 1/375* (2006.01)
(Continued)

(52) U.S. Cl.
CPC .......... *A61N 1/362* (2013.01); *A61N 1/3756* (2013.01); *A61N 1/37205* (2013.01); *A61B 17/3468* (2013.01)

(58) Field of Classification Search
CPC .. A61N 1/362; A61N 1/37205; A61N 1/3756; A61B 17/3468
(Continued)

(56) References Cited

U.S. PATENT DOCUMENTS 4,582,056 A  4/1986  McCorkle
6,185,464 B1  2/2001  Bonner
(Continued)

OTHER PUBLICATIONS

International Search Report and Written Opinion, PCT/US2010/037557, dated Oct. 29, 2010.

*Primary Examiner* — Michael Carey
(74) *Attorney, Agent, or Firm* — Moazzam & Associates, LLC (57) ABSTRACT

The present invention provides a fully intrathoracic artificial pacemaker. The pacemaker is of sufficiently compact size to allow for implantation of both the electrode and the power source within the chest cavity. In exemplary embodiments, a screw-type electrode is used for connection to heart tissue, and a relatively short lead is used to connect the electrode to a battery unit, which can comprise electronics for control of the pacemaker. An assembly for implanting the pacemaker, as well as methods of implanting the pacemaker, are disclosed. In embodiments, the device is designed as a fetal pacemaker.

13 Claims, 3 Drawing Sheets

Related U.S. Application Data

(60) Provisional application No. 61/184,329, filed on Jun. 5, 2009.

(51) Int. Cl.
*A61N 1/372* (2006.01)
*A61B 17/34* (2006.01)

(58) Field of Classification Search
USPC .................. 607/4, 9, 36, 119, 122, 126, 127
See application file for complete search history.

(56) References Cited

U.S. PATENT DOCUMENTS

| | | | |
|---|---|---|---|
| 9,126,047 B2* | 9/2015 | Bar-Cohen | A61N 1/362 |
| 2003/0204217 A1 | 10/2003 | Greatbatch | |
| 2006/0085041 A1* | 4/2006 | Hastings | A61N 1/0587 607/33 |
| 2007/0016276 A1* | 1/2007 | Heil, Jr. | A61N 1/362 607/119 |
| 2007/0293904 A1* | 12/2007 | Gelbart | A61N 1/3785 607/35 |

\* cited by examiner

ARTIFICIAL CARDIAC PACEMAKER DEVICE ASSEMBLY

CROSS-REFERENCE TO RELATED APPLICATIONS

This application is a divisional application of U.S. patent application Ser. No. 13/375,983, now U.S. Pat. No. 9,126, 047, filed 2 Dec. 2011, which is a U.S. National Stage application of PCT/US2010/037557, filed 5 Jun. 2010, which relies on and claims the benefit of the filing date of U.S. provisional patent application No. 61/184,329, filed 5 Jun. 2009, the entire disclosure of which is hereby incorporated herein by reference.

BACKGROUND OF THE INVENTION

Field of the Invention

The present invention relates to the fields of medicine and medical devices. More specifically, the present invention relates to pacemakers suitable for use in patients in need, including fetuses, and methods of using them to maintain an adequate heart rate in the patients.

Description of Related Art

Various devices for artificially providing an electrical impulse to cause or assist in the regular beating of a heart are known in the art. Such devices, commonly referred to as "cardiac pacemakers", "artificial pacemakers", or simply "pacemakers", have evolved from the relatively rudimentary electrical devices of the late 1950s and the 1960s to the highly sophisticated, programmable devices that are now available. Although there is variation in design and implementation of pacemakers, in general, all of them have a common function: to provide an electrical stimulus to cardiac muscle tissue to cause controlled, rhythmic contraction of the muscle tissue such that blood can be pumped through the heart, thus causing circulation of the blood throughout the body.

The design and use of cardiac pacemakers in adults are well established. In general, adult cardiac pacemakers consist of at least one conductive connector or electrode that attaches to heart tissue on one end and to an electrical lead on the other end. The lead is a relatively long conducting material that connects the electrode to a power supply, typically a lithium battery. Modern cardiac pacemakers include electronics to control the rate of pacing and to keep track of battery power, among other things. Typically, an adult cardiac pacemaker has a size on the order of 10 cc and has one or more leads of about 40-60 cm in length. There are several methods of implanting a pacemaker. These methods include those for epicardial pacing, which involves placing the electrodes in contact with the outer wall of the ventricle (epicardium) to maintain satisfactory pacing. Epicardial pacing is the pacing method of choice for babies because their veins are considered too small for a transvenous system. In contrast, transvenous cardiac pacing, also called endocardial pacing, involves inserting a wire containing an electrode lead into a vein, preferably the subclavian vein, and passing it through the vein to either the right atrium or right ventricle. The procedure is facilitated by fluoroscopy, which enables the physician or cardiologist to view the passage of the electrode lead. Permanent pacing with an implantable pacemaker involves connecting the opposite end of the electrode lead and wire to the pacemaker generator (battery and control unit). The pacing generator, or control/battery unit, is then surgically implanted into the patient's chest (for transvenous systems) or the abdomen (for epicardial systems). In transvenous systems, the entire implanted pacemaker thus includes a relatively long lead that runs from the heart, through a vein, and to a battery pack/control unit implanted in the patient's chest.

While design and use of adult pacemakers is a mature field, the same cannot be said for the design and use of fetal pacemakers. Rather, the field of fetal pacemakers has yet to show a successful design and implementation. To date, fetal pacemakers have been designed based on the same concepts used for adult pacemakers. That is, designs for fetal pacemakers have employed an electrode and long lead connected to a battery unit. The electrode is contacted with the fetal heart tissue, and the battery unit is placed outside of the uterus. Such a design has uniformly met with rapid failure due to movement of the fetus in the uterus, which causes dislodgement of the electrode from the fetal heart tissue.

SUMMARY OF THE INVENTION

The present inventors have recognized the need in the art for improved fetal cardiac pacemakers, and have developed a solution for that need. In doing so, the inventors have also developed an improved cardiac pacemaker that is suitable for use in infants, children, and adults. The present invention provides a cardiac pacemaker that can provide artificial electrical stimuli for sustained rhythmic beating of a heart. Where designed for use in a fetus, the pacemaker can be implanted in utero without significant harm to the developing fetus or the mother, and can function for extended periods of time without dislodging or otherwise failing. Where designed for infants, children, or adults, the pacemaker can be implanted quickly and under conditions that might otherwise preclude successful implantation of a pacemaker. Like the fetal pacemaker, the pacemaker for infants, children, and adults can be implanted without significant harm to the patient and can function for extended periods of time. In the disclosure that follows, particular attention is paid to embodiments relating to fetuses because the design of the pacemaker is particularly well suited and advantageous for use in fetuses. However, it is to be understood that the concepts and details discussed are equally applicable to design and implementation of the invention as it relates to other patients.

In a first aspect, the invention provides a fully implantable cardiac pacemaker. The pacemaker of the invention includes one or more relatively short leads (also referred to herein as "wires") that connect a source of power to electrodes (also referred to herein as "coils") implanted in the heart muscle tissue. The power source can include electronics for control of the device, reporting of performance of the device, and other things. Unlike fetal pacemakers attempted in the past, the present pacemaker, where designed for use in a fetus, is fully implantable in the fetus, and thus avoids problems associated with movement of the fetus within the uterus causing dislodgement of the electrodes from the fetal heart. Providing a pacemaker that can be fully contained within the body of a fetus overcomes a key obstacle in fetal pacemaker art.

The pacemaker device of the invention can be provided as part of a device assembly for implantation of the device into a chest cavity, such as a fetal chest cavity. In general, the device assembly comprises a pacemaker device releasably attached to means for deploying the pacemaker device into a chest cavity. The device and insertion means are releasably attached to each other by way of a wire, thread, string, or other similar structure, referred to herein as a "holder". Typically, the device assembly comprises a distal region comprising the pacemaker device and a proximal region comprising the means for deploying the pacemaker device into the body of a patient. The pacemaker device comprises at its distal end at least one electrode (e.g., a screw-type electrode) for connecting the device to fetal heart tissue. The electrode is attached to a relatively short wire or lead that connects the electrode to a power source (e.g., a battery pack) located on the proximal end of the device. The power source also comprises a controller (e.g., a computer chip for controlling emission of electrical impulses from the power source). Located proximal and releasably attached to the pacemaker device is a structure for deploying the pacemaker into the body of a patient. For ease of reference, this structure is referred to herein as a "pusher". The pusher is a relatively long rod-like element that has a diameter or width similar to or the same as the diameter or width of the pacemaker device, and which is sized to fit within the lumen defined by the inner surface of the trocar to be used in conjunction with the assembly. The pusher is of sufficient length to allow for inserting of the pacemaker device into the chest cavity of a patient, such as into the chest cavity of a fetus from a point outside of the mother's body. In embodiments, the device assembly further comprises a housing, such as a tube (e.g., a trocar), having an exterior surface defining the outside of the assembly, and having an interior surface defining a lumen of the assembly housing in which the pacing device, pusher, and holder are located.

The present invention further provides a method for implanting a cardiac pacemaker into a patient, such as a fetus. In general, the method comprises inserting a device assembly through a trocar into the chest cavity of the patient to the point where the device assembly touches heart tissue at a pre-selected location. Preferably, the trocar is inserted through the right side of the chest. After insertion of the trocar, a device assembly according to the invention is inserted into the interior space of the trocar through its proximal end. Using the pusher, the device assembly is passed longitudinally through the trocar to the point where the distal end of the pacemaker device (i.e., the electrode) touches heart tissue. The electrode is then implanted in the heart tissue. Upon implantation, the heart is monitored for pacing provided by the device. Upon confirmation of proper pacing, the device assembly is disassembled to release the pacemaker device from the remaining components of the device assembly, and to fully deploy the pacemaker device. In doing so, the pacemaker device is released from the pusher by disabling the holder. The holder and pusher are removed from the trocar and the trocar is removed from the body, leaving the pacemaker fully in the chest. If necessary or desired, the pacemaker device can be pushed out of the housing through physical movement of the pusher against the pacemaker device prior or during removal of the trocar from the chest. The power source/control unit of the device is typically designed to fit snugly against the inner wall of the trocar (or device housing, if present), but not so snugly as to preclude sliding of the control unit through the trocar during deployment. During retraction of the housing and after deployment of the pacemaker device, the power source/control unit is deployed in the thoracic cavity. If necessary or desired, the power source/control unit can be pushed out of the housing and into the thoracic cavity through physical movement of the pusher against the power source/control unit. Process steps for implantation of the pacemaker can be followed using any known technique, including fiber optic visualization, use of non-invasive radiation (e.g., real-time X-ray imaging, etc.), ultrasound, and the like.

Yet further, the present invention provides a method for artificially pacing a heart, such as a fetal heart. According to the method, a fully implantable pacemaker according to the invention is implanted in the body of a patient and the pacemaker is connected to heart tissue. Electrical impulses from the pacemaker cause artificial pacing of the heart. In embodiments, artificial pacing is achieved for at least one week. In preferred embodiments, artificial pacing is achieved for at least two weeks. In some embodiments, artificial pacing is achieved for at least two months. The method is highly suitable for artificial pacing of fetal hearts for any reason, including complete heart block or hydrops fetalis. The method is achieved by a fully implanted, closed system entirely within the chest and implanted with a minimally invasive technique. These attributes make the invention highly advantageous for applications involving fetuses.

The present invention includes pacemakers, methods of implanting pacemakers, and methods of using pacemakers in patients of all stages of development and of all ages. That is, the concepts discussed herein are generally applicable to infants, children, and adults as well as fetuses. For example, a pacemaker device according to the invention can be used for pacing in children and adults who might require urgent pacing or where venous access issues make implantation using standard pacing methods difficult. The pacing device (with pusher and holder) can be implanted into an infant's, child's, or adult's chest via a housing or sheath introduced through the chest wall. For example, the pleural or pericardial cavities can be accessed via a needle through the chest wall using well-known techniques, followed by placement of chest tubes or pigtail catheters as required. The tip of the housing or sheath can then be pushed up against the ventricular myocardium and the pacing device implanted by advancing a device assembly to the tip of the housing or sheath (if necessary), then screwing the entire mechanism (device plus pusher) into the myocardium. When pacing is confirmed, the housing or sheath (as well as pusher) can be removed from the body and allow pacing of the heart for days to weeks (or longer if necessary or desired). The invention thus provides an implantable pacing system that allows for pacing in patients of all ages for an extended period of time.

BRIEF DESCRIPTION OF THE DRAWINGS

The accompanying drawings, which are incorporated in and constitute a part of this disclosure, illustrate features of embodiments of the invention, and together with the written description, serve to explain certain principles of the invention. The accompanying drawings are provided as examples of the present invention, and are not to be construed as limiting the scope or content of the invention.

DETAILED DESCRIPTION OF VARIOUS EMBODIMENTS OF THE INVENTION

Reference will now be made in detail to various exemplary embodiments of the invention, examples of which are illustrated in the accompanying drawings. It is to be understood that the following detailed description is provided to give the reader a better understanding of certain details and features of embodiments of the invention, and that the following description is not to be understood as a limitation on the scope of the invention.

One general aspect of the invention is a fully-implantable cardiac pacemaker. In the exemplary embodiment discussed now, the pacemaker relates to a fetal pacemaker, with the understanding that the concepts, materials, and techniques are equally applicable to patients after birth. The pacemaker of this exemplary embodiment of the invention comprises at least one electrode for delivering an electric pulse to fetal cardiac tissue. The electrode can be fabricated from any suitable material or combination of materials that are electrically conductive, and is typically fabricated from one or more metals. Suitable materials are known and widely used in the art. The electrode comprises a connector that connects the electrode to fetal cardiac tissue on one end and to an electrically conductive lead (also referred to herein as a wire) on the other end. While not limited in design, in exemplary embodiments, the connector is provided in the shape of a coil or screw, which is capable of being embedded in fetal cardiac tissue through a twisting motion. Connectors that are suitable for use in the pacemaker device of the invention are known in the art, and any such connector may be used.

The pacemaker further comprises one lead per electrode to connect the electrode to a power source. The lead can be fabricated from any suitable material or combination of materials that are electrically conductive. Typically, the lead is fabricated from one or more metals, as known in the art. Typically, the lead further comprises an insulative material around the electrically conductive material(s) along the length of the lead to prevent transmission of electricity except through the ends of the lead. Leads that are suitable for use in the pacemaker device of the invention are known in the art, and any such lead may be used. It is to be recognized that, in contrast to leads used in prior attempts to develop fetal cardiac pacemakers, the leads of the present invention are relatively short. That is, in contrast to prior attempts, rather than providing a relatively long lead (e.g., about 10 cm-15 cm in length) that can span a distance from the fetal heart to the mother's abdomen, the present device comprises a lead that is designed to span only the distance from the fetal heart to the fetal chest cavity (e.g., about 2 cm-3 cm). Likewise, because a fully-intrathoracic pacemaker design for children and adults has not been devised before, the leads for pacemakers of those embodiments are likewise relatively short, such as on the order of 5-10 mm.

The fetal pacemaker device further comprises a power source connected to one end of the lead(s). The power source provides electrical energy to the electrode(s) and, where present, to a controller unit. The power source is not limited in design or composition. However, in exemplary embodiments, the power source is a battery or set of batteries in electrical connection with each other. In embodiments, the power source comprises a non-conducting covering. The size of the power source can vary depending on the life stage of the patient to be treated and the length of time that pacing is desired. In general, the power source is designed to fit in the chest cavity or thorax of a fetus, child, or adult to be treated. While not limited in size, in general the power source for fetal applications will be about 4 mm or less in diameter or width and 1 cm or less in length. For example, it can be from 1 mm to 4 mm in diameter, such as 2 mm, 3 mm, or 4 mm. Likewise, the power source can have a length of from 5 mm to 1 cm, such as 5 mm, 6 mm, 7 mm, 8 mm, 9 mm, or 1 cm. Further, while not limited in size, in general, the power source for child applications will be about 4-10 mm or less in diameter or width and 1-3 cm or less in length. Where desired, two or more individual batteries can be connected in series or in parallel to achieve the desired longevity, voltage, etc. Selection of the appropriate battery size, shape, and power will be made by the practitioner after consideration of the amount of energy needed to pace the fetal heart, the point in gestation of the fetus, the type of pacing and number of electrodes needed, the length of desired time for functionality, and other parameters of interest to the practitioner. Many of the same considerations are relevant to child and adult pacemakers, with the understanding that, with increasing size of the patient, larger components may be used. Use of larger components can provide additional longevity and power to the pacemaker device.

In preferred embodiments, the pacemaker device further comprises a control unit that controls the frequency and power of impulses sent to the cardiac tissue. In general, the control unit comprises electronics. Control units for pacemakers are known in the art, and any suitable design can be used. In preferred embodiments, the control unit is programmed to alter the frequency of pacing when the power source reaches a pre-defined point of remaining stored energy. For example, a controller can pace a fetal heart at 100 beats per minute. However, when the controller senses that the power source has only, for example, thirty-six hours of power life left, the controller slows the pacing to 90 beats per second. This drop in heart rate can easily be detected by the mother's obstetrician, and he can take an appropriate action (e.g., induce labor, add an additional pacemaker). The control unit will have a size similar to the power source. In embodiments, the two are combined as a single functional unit having a size according to the description above for the power source.

Another general aspect of the invention is a device assembly for implantation of the pacemaker device into a chest cavity. In general, the device assembly comprises a pacemaker device for artificial pacing of a heart, a pusher for implanting the device into a patient, and a holder that holds the pacemaker device and pusher together. While not limited in size, in general, the assembly is designed to fit within the inner diameter of a trocar that is suitable for use in surgery for the patient of interest, or within a device housing. Thus, in general, the device assembly has a diameter or width of about 4 mm or less, such as from 4 mm to 1 mm, for example 4 mm, 3 mm, 2 mm, or 1 mm. Likewise, in general, the device assembly has a length of about 10 cm-15 cm or more for fetal applications. Thus, in embodiments, the device assembly has a length of 10 cm, 11, cm, 12 cm, 13 cm, 14 cm, or 15 cm. Longer lengths, such as 20 cm or 25 cm are also contemplated. In general, the device assembly has a diameter or width of about 4 mm to 10 mm or less, and a length of about 1 cm to 3 cm or more for child and adult applications. The practitioner may select any particular value falling within these ranges based on various considerations.

The assembly comprises a distal portion that is defined by a pacemaker device of the invention. Located proximal and releasably attached to the pacemaker device is a pusher. The pusher is a relatively long rod-like element for inserting the pacemaker device or the full device assembly into and through a housing from its proximal end outside of a patient's body to its distal end within the chest cavity of the patient. For fetal applications the length is sufficient to extend from the proximal end outside of the mother's body to its distal end within the fetal chest cavity.

The pusher may be fabricated out of any suitable material, and is preferably made from a material that can be easily sterilized. For example, the pusher may be made from one or more plastic materials known in the art as suitable for medical devices. The pusher is preferably, but need not necessarily be, made from a disposable material, such as known for single-use in medical procedures.

The device assembly further comprises a holder. The holder functions to releasably connect the pusher to the pacemaker. The holder can be any element that releasably connects the pusher to the pacemaker, and can take any shape or size. In exemplary embodiments, the holder is a string, thin wire, or elastic band that sits in a two opposing grooves cut along the walls of the pusher and power source of the pacemaker. When employed, the holder physically holds the pusher and pacemaker together, such that they substantially form a single unit. When desired (e.g., when the pacemaker is implanted), the holder is cut, thus releasing the pacemaker from the pusher.

The present invention uses the device assembly to provide a method for implanting a cardiac pacemaker into a patient. The method permits full implantation of a pacemaker device into a patient, and provides a significant improvement in artificial cardiac pacing, including in both fetuses and in children or adults, particularly in situations where a child or adult is in need of urgent pacing and other pacing device designs are incapable of being implanted quickly and effectively. In general, the method comprises inserting a trocar into the chest cavity of a patient. A device assembly according to the invention is then inserted into the interior space of the trocar to the point where the electrode touches heart tissue. The electrode is then implanted in the heart tissue, the holder is cut, and the holder and pusher are removed. The device assembly housing is retracted from the chest cavity while implanting the power source and controller in the chest cavity. That is, after implantation of the electrode into the heart, the holder is cut and the housing is retracted while deploying the remaining portion of the pacemaker device into the chest cavity using, if necessary, the pusher to move the device out the distal end of the housing. Where appropriate, the entry points for the trocar (e.g., mother's abdomen) are closed using standard techniques.

While various parameters and method steps may be altered to suit particular purposes, the present disclosure provides both general and specific guidance on practicing the invention. Those of skill in the art will recognize variations and modifications to the specifically disclosed embodiments that fall within the general teachings of the present document. For example, the present disclosure discusses batteries as a power source for the pacemaker device. Those of skill in the art will recognize that the shape of the battery is not critical, as long as it does not interfere with deployment of the device within the patient or with function of the device. Thus, the battery may take any cross-sectional geometry, such as round, square, or rectangular.

While embodiments relating to fetal pacing provide significant improvements in treatment for such patients, other embodiments of the invention relate to pacemakers for patients after birth, and such embodiments provide significant improvements in treatment of such patients. In all embodiments, the device is a complete pacing system that can be implanted within the thorax without invasive surgery or the need for transvenous access. For example, in urgent situations relating to children and adults where ventricular pacing is necessary and vascular access cannot be easily achieved, the device can be inserted into myocardium and allow for temporary pacing until a permanent pacing system can be implanted. Likewise, the device of the invention can be used to treat adults who present with significant bradycardia and require urgent pacing.

The device of the invention can also be used in adults who require extended pacing and in whom standard transvenous or epicardial systems cannot be implanted. As is known in the art, emergency pacing can currently be performed by transcutaneous pacing (by use of large pads on the chest), but this make ventilation extremely difficult and is not always effective—it can generally only be used for a short period of time. When more prolonged pacing is required (e.g., around 24 hours), a temporary pacing lead is placed (through the veins) and is pushed up against the ventricular myocardium. This technique, however, requires vascular access and a degree of expertise in catheter manipulation to access the ventricle. In contrast to the current commonly available technologies, the present invention allows pacing for weeks to months, if necessary or desired, with a pacemaker that can be implanted without vascular access and in an urgent fashion.

Reference will now be made to an exemplary pacemaker device and device assembly according to the invention. The exemplary embodiments discussed are depicted in the figures.

Figure 1:
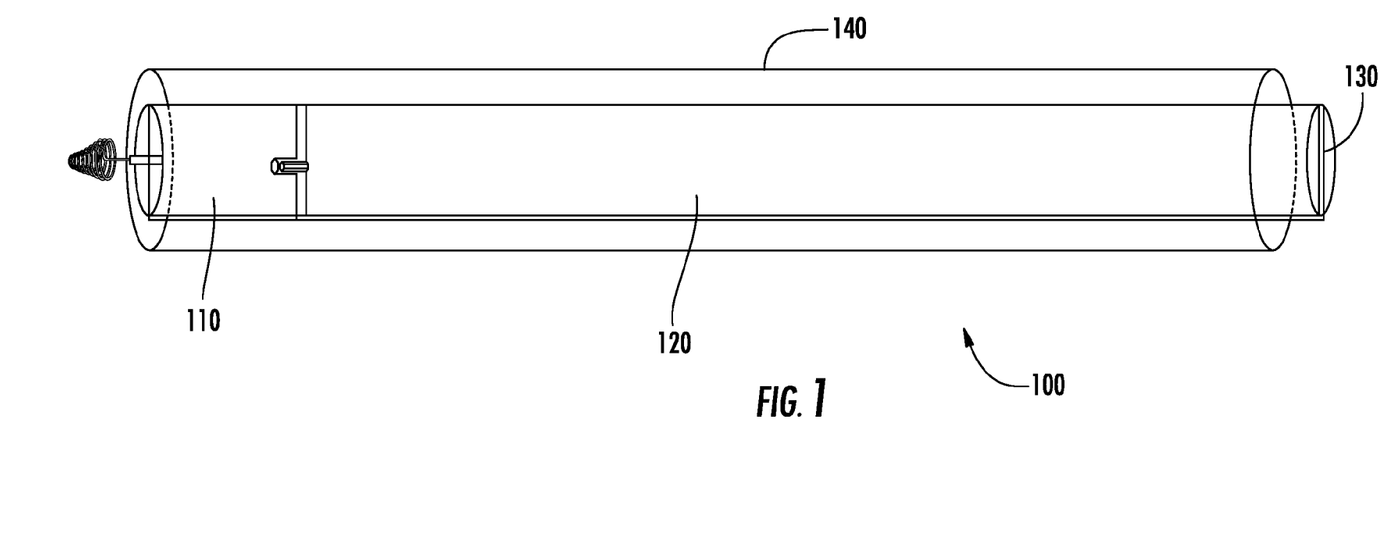
FIG. 1 depicts an embodiment of the device assembly according to one aspect of the invention, which is disposed within the central lumen of a device assembly housing.

With reference to FIG. 1, a device assembly 100 is generally depicted within the interior of a housing 140. Device assembly 100 includes pusher 120, pacemaker device 110, and holder 130. It is to be noted that the diameter of the device assembly is reduced in the figure solely for the purpose of improved clarity of the drawing. As disclosed above, the device assembly will typically have a diameter or width only slightly smaller than the inside diameter or width of the housing to be used.

Figure 2:
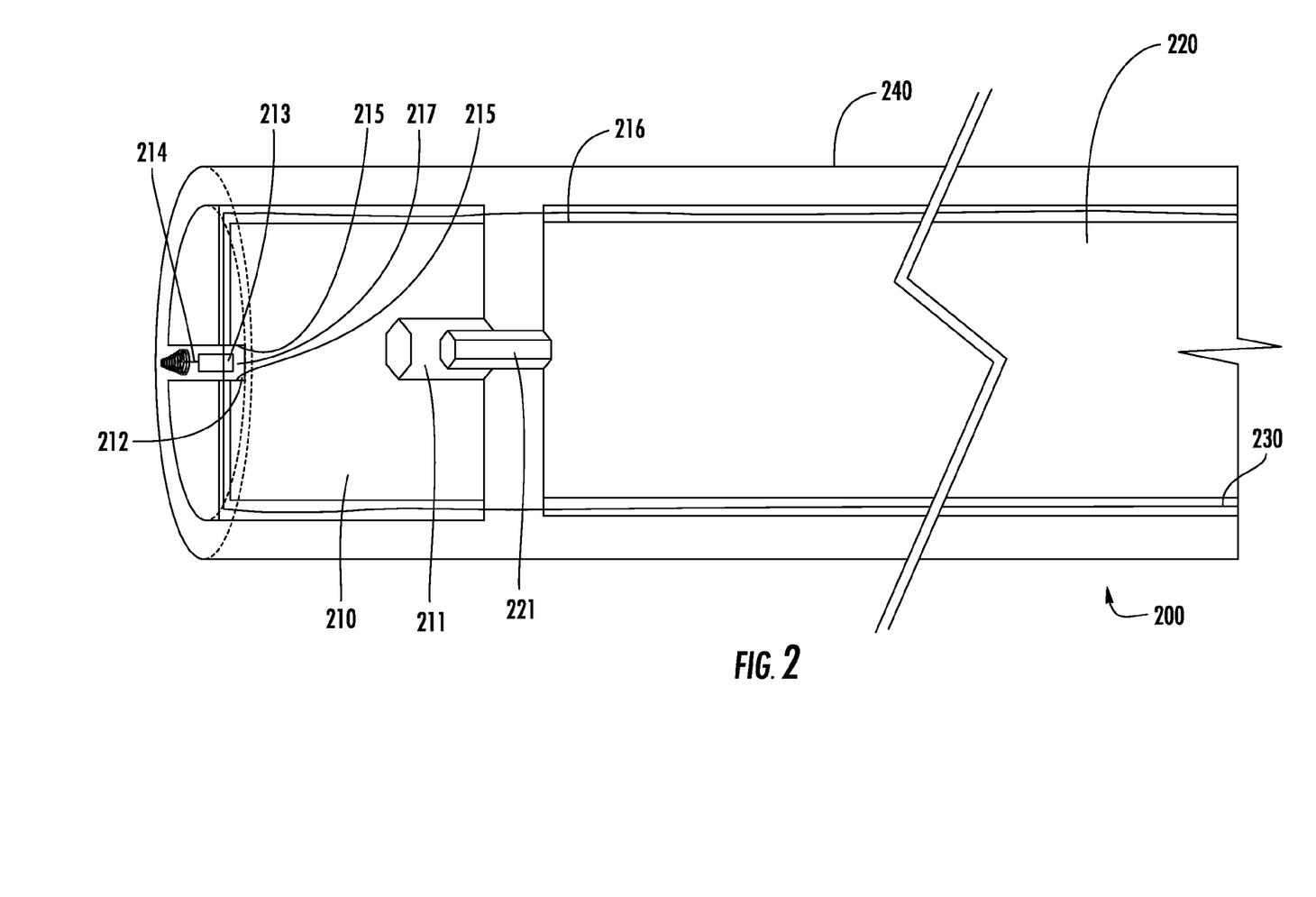
FIG. 2 depicts the embodiment of the device assembly according to FIG. 1, showing additional detail regarding structural features of the pacemaker device, the pusher, and the holder.

With reference to FIG. 2, a more detailed view of device assembly 200 is shown. As in FIG. 1, FIG. 2 depicts device assembly 200 disposed within the inner lumen of housing 240. Device assembly 200 includes pusher 220, pacemaker 210, and holder 230. Holder 230 is disposed within groove 216, which comprises an open space on two diametrically opposed sides of pusher 220 and pacemaker 210 that can accommodate holder 230. Pusher 220 further comprises male connector 221 for rotationally locking pusher 220 and pacemaker 210 such that neither is free to rotate, with respect to the other, about a longitudinally central point. The figure depicts male connector 221 having a hexagonal cross-section. However, it is to be noted that any suitable non-circular cross sectional shape can be used, including, but not limited to, triangular, square, rectangular, pentagonal, octagonal, star-shaped, and elliptical.

As further shown in FIG. 2, device assembly 200 includes pacemaker device 210 with several structural elements. Pacemaker device 210 comprises female connector 211 for rotationally locking pacemaker 210 and pusher 220. It is to be recognized that the size of female connector 211 is determined in conjunction with the size of male connector 221 such that male connector 221 is not free to rotate within the space defined by female connector 221. In practice of an exemplary method for implanting a pacing device according to the invention, rotational locking of pusher 220 and pacemaker 210 allows transmission of twisting performed on the pusher 220 by the practitioner outside the body (e.g., outside a mother's abdomen) to pacemaker 210. In embodiments where pacemaker 210 comprises a screw or coil-like connector (as shown in FIGS. 1-3), the twisting motion allows the practitioner to embed the connector into the heart tissue.

Further with reference to FIG. 2, pacemaker 210 comprises structures for storing and deploying an electrode. More specifically, pacemaker 210 comprises recess 212 that can house lead 217, which is connected to coil retention mechanism 213 and the body of pacemaker 210. Holder 230 is disposed within groove 216 on pusher 220 and pacemaker 210 and through a conduit (not depicted in FIG. 2; depicted as element 318 in FIG. 3) in coil retention mechanism 213. Placement of holder 230 through the conduit and along groove 216 permits holder 230 to retain pacemaker device 210 in connection with pusher 220. It is to be noted that, in the figures, the pusher and pacemaker device are depicted as not being in physical contact with each other. The depiction is for clarity purposes only—the two elements are in physical contact with each other when provided as parts of an assembly. Further, while not shown with particularity in the figures, recess 212 and coil retention mechanism 213 are designed to have cross-sections that permit rotational locking of the two. That is, similar to male connector 221 and female connector 211, recess 212 and coil retention mechanism 213 have cross-sections that interconnect and preclude rotational freedom between the two. In this way, a twisting motion imparted on pusher 220 outside a patient's body (e.g., outside a mother's abdomen) is translated to a twisting motion through the body of pacemaker 210 and to electrode 214. Where a coil- or screw-type connector is used as part of electrode 214, the twisting imparted outside the body results in implantation of the electrode in cardiac tissue.

Pacemaker device 210 further comprises seat 215, which blocks coil retention mechanism 213 from fully entering recess 212 and provides adequate space for lead 217 during storage. In the exemplary embodiment, lead 217, which connects electrode (which in the embodiments depicted in the figures is a coil or screw) 214 with the battery of pacemaker 210, can be bundled within recess 212. When holder 230 is cut and removed after implantation of electrode 214 into cardiac tissue, electrode 214, coil retention mechanism 213, and lead 217 extend away from the body of pacemaker 210.

Figure 3:
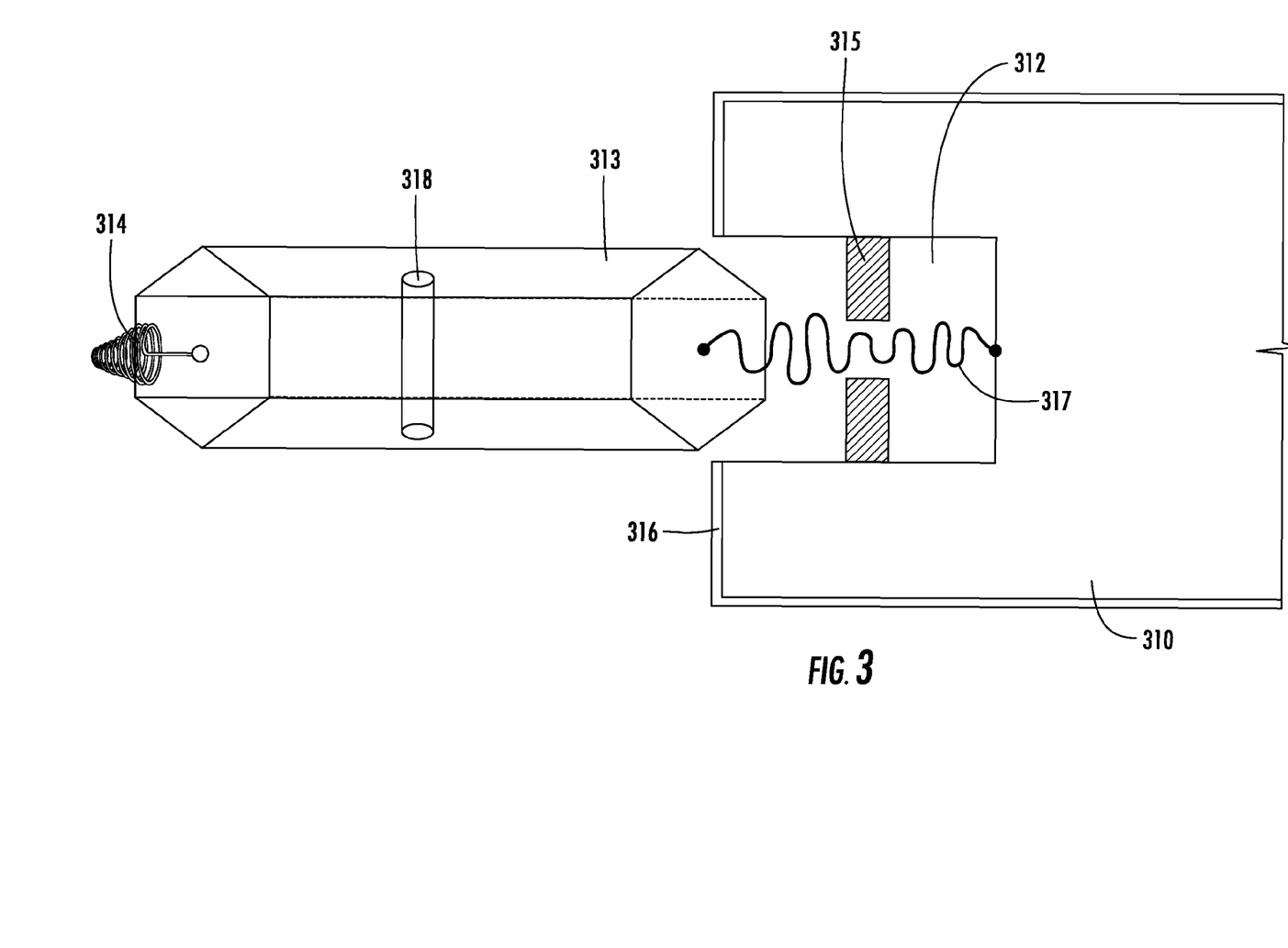
FIG. 3 depicts an embodiment of the pacemaker device after implantation into cardiac tissue and release from the device assembly.

Turning now to FIG. 3, an example of a partially-deployed pacemaker 310 is depicted. The figure depicts pacemaker 310 after implantation of electrode 314 into cardiac tissue, but before final placement of pacemaker 310 into the chest cavity. For the purpose of clarity, no housing is depicted. As can be seen in the figure, the holder has been removed from groove 316 and conduit 318, and coil retention mechanism 313 is no longer in contact with seat 315 and has exited recess 312. Lead 317 is partially unbundled as a result of movement of coil retention mechanism 313 away from recess 312. In the figure, lead 317 is depicted as having a short length; this is for the purpose of clarity of the drawing only. It is to be noted that the length of lead 217 can be any suitable length that allows for placement of the body of pacemaker 310 in the chest cavity of the patient while attaching electrode 314 to the appropriate locus in the epicardium. Likewise, for the sake of clarity, coil retention mechanism 313 is depicted as relatively long; however, the length can be any length that is appropriate and useful. Likewise, while the cross-section of coil retention mechanism 313 is depicted as hexagonal, any suitable cross-sectional shape can be used.

It will be apparent to those skilled in the art that various modifications and variations can be made in the practice of the present invention and in construction of this device without departing from the scope or spirit of the invention. Other embodiments of the invention will be apparent to those skilled in the art from consideration of the specification and practice of the invention. For example, the device assembly can include a device housing or other outer structure that retains the pacemaker device, power/control unit(s), pusher, and holder. It is intended that the specification and examples be considered as exemplary only, with a true scope and spirit of the invention being indicated by the following claims.

The invention claimed is:

1. An artificial cardiac pacemaker device assembly, said assembly comprising:
   an artificial cardiac pacemaker with a recess structure having a non-circular cross-section;
   a pusher for deploying the cardiac pacemaker into heart tissue and having a complementary structure which corresponds to the recess structure of the artificial cardiac pacemaker, wherein rotational locking of the complementary structure of the pusher with the recess structure of the artificial cardiac pacemaker allows transmission of a twisting motion performed on the pusher; and
   a holder for releasably holding the artificial cardiac pacemaker and pusher in physical contact.

2. The assembly of claim 1, wherein the artificial cardiac pacemaker and pusher have circular cross-sections having the same diameter of 4 mm or less.

3. The assembly of claim 1, wherein the artificial cardiac pacemaker has a length of 1 cm or less and the pusher has a length of 10 cm to 15 cm.

4. The assembly of claim 1, having a tubular shape with a diameter of 4 mm or less and a length of 10 cm to 15 cm.

5. The assembly of claim 1, wherein the assembly is of sufficient length to pass through the abdomen of a pregnant woman and make contact with heart tissue of a gestating fetus within the woman.

6. A method of implanting an artificial cardiac pacemaker in a patient, said method comprising:
   inserting a trocar into the chest cavity of the patient;
   inserting the cardiac pacemaker device assembly of claim 1 into the inner lumen of the trocar to the point where the artificial cardiac pacemaker contacts the patient's heart tissue;
   attaching the artificial cardiac pacemaker to the heart tissue;
   releasing the artificial cardiac pacemaker from the pusher;
   positioning the power source and control unit of the artificial cardiac pacemaker in the chest; and
   removing the trocar from the patient,
   wherein release of the artificial cardiac pacemaker from the pusher and removal of the trocar results in implantation of the artificial cardiac pacemaker device fully within the body of the patient.

7. The method of claim 6, wherein the patient is a gestating fetus, said method comprising:
   inserting a trocar through the abdomen of a pregnant woman and into the chest cavity of the gestating fetus;
   inserting the artificial cardiac pacemaker device assembly into the inner lumen of the trocar to the point where the artificial cardiac pacemaker contacts fetal heart tissue;
   attaching the artificial cardiac pacemaker to the fetal heart tissue;
   releasing the artificial cardiac pacemaker from the pusher;
   positioning the power source and control unit of the artificial cardiac pacemaker in the fetal chest; and
   removing the trocar from the fetus and the woman, wherein release of the artificial cardiac pacemaker from the pusher and removal of the trocar results in implantation of the artificial cardiac pacemaker device fully within the body of the fetus.

8. The method of claim 6, wherein attaching the artificial cardiac pacemaker to the heart tissue comprises using the pusher to advance the pacemaker through the trocar to the point where the electrode of the artificial cardiac pacemaker contacts the heart tissue.

9. The method of claim 6, wherein attaching the artificial cardiac pacemaker to the heart comprises rotating the pusher to cause the electrode of the artificial cardiac pacemaker to embed into the heart tissue.

10. The method of claim 6, wherein positioning the power source and control unit in the chest comprises using the pusher to push the power source and control unit out the end of the trocar and into the chest cavity.

11. The method of claim 6, further comprising removing the pusher from the trocar after positioning the power source and control unit in the chest and before fully removing the trocar from the chest.

12. The assembly of claim 1, wherein the artificial cardiac pacemaker further comprises a lead, an electrode, and a power source, and includes a mechanism for retaining the lead and the electrode in close proximity to the power source until the artificial cardiac pacemaker is implanted and functioning.

13. The assembly of claim 1, wherein the holder comprises one or more of a wire, a thread, or other similar structure.

* * * * *